United States Patent [19]

Soled et al.

[11] Patent Number: 5,100,856
[45] Date of Patent: Mar. 31, 1992

[54] IRON-ZINC BASED CATALYSTS FOR THE CONVERSION OF SYNTHESIS GAS TO ALPHA-OLEFINS

[75] Inventors: Stuart L. Soled; Sabato Miseo, both of Pittstown; Enrique Iglesia, Clinton; Rocco A. Fiato, Basking Ridge, all of N.J.

[73] Assignee: Exxon Research and Engineering Company, Florham Park, N.J.

[21] Appl. No.: 591,304

[22] Filed: Oct. 1, 1990

[51] Int. Cl.$^5$ .................... B01J 23/72; B01J 23/78; B01J 23/80
[52] U.S. Cl. .................................................. 502/329
[58] Field of Search ........................................ 502/329

[56] References Cited

U.S. PATENT DOCUMENTS 4,199,523 4/1980 Rottig .................................. 518/713
4,478,955 10/1984 Pesa et al. ...................... 502/329 X

OTHER PUBLICATIONS

Benbenek et al., Prezm Chem., vol. 65(3), pp. 136–138 (1986).

*Primary Examiner*—W. J. Shine
*Attorney, Agent, or Firm*—Jay Simon

[57] ABSTRACT

New copper-potassium promoted iron-zinc catalysts wherein the iron:zinc atomic ratio is 5:1 or greater, exhibit improved activity, selectivity and stability in the synthesis of alpha-olefins from hydrogen and carbon monoxide.

5 Claims, No Drawings

IRON-ZINC BASED CATALYSTS FOR THE CONVERSION OF SYNTHESIS GAS TO ALPHA-OLEFINS

FIELD OF THE INVENTION

This invention relates to iron-zinc based catalysts containing copper and a Group I metal promoter, and their use in a process for the conversion of synthesis gas to alpha olefins.

BACKGROUND OF THE INVENTION

The search for processes to provide alternate feedstocks for chemicals, and particularly low to intermediate range olefins, has been prompted by the potential shortage of traditional petroleum reserves, and the increasing instability of international hydrocarbon resources.

One approach to the problem has been the utilization of the Fischer-Tropsch synthesis in producing a selective product distribution of olefinic hydrocarbons also containing paraffins, in varying olefin/paraffin ratios, depending on the catalyst composition, pretreatment procedures, and reaction conditions. Catalysts having various combinations of elements have been tested in the past, and the chief constituent element of the catalyst has been nickel, cobalt, iron or ruthenium.

Ruhrchemie Aktiengesellachaft disclosed in GB No. 1,512,743, GB No. 1,553,361 GB No. 1,553,362 and GB No. 1,553,363 catalysts pertaining to the selective production of $C_2$-$C_6$ olefins from synthesis gas, comprising carbon monoxide and hydrogen. The inventions embody a process for the production of one or more unsaturated hydrocarbons comprising catalytic hydrogenation of carbon monoxide with hydrogen at 250° C. to below 350° C. and a total pressure of 10 to 30 bars in the presence of a catalyst which contains (a) one or more oxides selected from difficult-to-reduce oxides of metals from Group IVB of the Periodic Table or a lower oxide of Group V and/or Group VII; and (b) one or more metals selected from Group VIII of the Periodic table, the ratio by weight of the metal or metals of the one or more oxides (a) to the one or more oxides (b) being in the range 1:2 to 1:10. Additionally, the catalysts can contain a Group 1A alkali metal, MgO and ZnO promoters. Good yields of unsaturated hydrocarbons, especially gaseous olefins were reported with these catalysts.

U.K. Patent No. 833,976 discloses a catalyst for the production of ethylene from carbon monoxide and hydrogen consisting of four components: the first a group including zinc oxides; the second group preferably being cobalt, although iron also can be used, with the proviso that the Group VIII metal component constitute not more than 10% of the total weight of the catalyst, and being activated by compounds which may include manganese oxide; a third group including an oxide of titanium and/or the rare earth elements; and the fourth group being a carbonate, oxide or hydroxide of an alkali metal. The reaction preferably is conducted at a temperature of 350° C. to 520° C., preferably 350° C. to 450° C.

U.S. Pat. No. 4,199,523 discloses a Fischer-Tropsch catalyst containing at least 60% iron. In addition, promoters such as copper and/or silver and alkali are described. Other additives, such as alkaline earth metal compounds, zinc oxide, manganese oxide, cerium oxide, vanadium oxide, chromium oxide and the like may be used.

U.S. Pat. No. 4,639,431 discloses a Fischer-Tropsch catalyst containing iron, a Group IIB metal such as zinc, with Group IA metal promoters with a lanthanide metal such as cerium which is sintered at temperatures ranging from 800°-1200° C.

Benbenek et al in Prezm Chem, Vol 65 (3) pp. 136-138 (1986) disclose a four component catalyst for converting synthesis gas to olefins; the catalyst comprising iron:copper:zinc oxide:potassium oxide in a weight ratio of 100:20:10:8.

However, what is desired in the art and which none of the above-identified art disclosures teach is a catalyst which exhibits high activity in the production of $C_2$-$C_{20}$ alpha-olefins while concurrently maintaining high activity and selectivity under olefin producing conditions. Especially preferred is a catalyst which can generate high levels of alpha olefins in a hydrogen rich environment, where the $H_2$/CO molar ratio is 2/1 or higher, which is normally conducive to good activity maintenance but otherwise leads to a significant decrease in olefin/paraffin ratios.

SUMMARY OF THE INVENTION

Iron-zinc based catalysts containing copper and a Group I, preferably potassium, promoter wherein the ratio of iron:zinc components is about 5:1 or higher, exhibit enhanced activity and selectivity to alpha-olefins during Fischer-Tropsch olefin synthesis. These catalysts also maintain high olefin/paraffin ratios under slurry reaction conditions.

The olefin synthesis activity and selectivity of these catalysts can be enhanced greatly when the alkali:copper promoter ratio is 1:1 or greater, preferably at least about 2:1, and the total alkali content of the catalyst is about 6% g-atom or lower, based on the total metal content of the catalyst.

These catalysts may be prepared by controlled pH precipitation of solutions containing soluble iron an zinc compounds with ammonium carbonate or ammonium hydroxide or via decomposition of iron-zinc containing ammonium glycolate complexes. The preparation of the catalyst employed in this invention may be initiated from a variety of precursors. Preferred precursors are the nitrate salts of iron and zinc, although carbonyls and carboxylates may also be used.

DESCRIPTION OF THE PREFERRED EMBODIMENTS

The active catalyst is prepared from an iron-zinc containing oxide phase, wherein the relative Fe:Zn atomic ratio is about 5:1 or greater. Thus, if the oxide phase is a spinel $Fe_{3-x}Zn_xO_4$, the ratio $[3-x]/x$ is equal to or greater than 5/1, and if the oxide contains iron in a corundum phase, isomorphous with $Fe_2O_3$, the ratio of Fe:Zn is equal to or greater than 5/1. Catalysts derived from mixed oxide phases wherein the total Fe:Zn atomic ratio is in the specified range are expected to give acceptable performance, although it is preferred to operate with a single phase catalyst precursor so as to preclude any irregular behavior in subsequent activation procedures.

Copper and alkali promoters are added to the iron-zinc oxide precursor, the copper preferably being added as a solution of the nitrate salt, although other copper compounds such as carboxylates may be used, and the alkali metal preferably being added as a solution of the carbonate, bicarbonate or hydroxide. Preferred alkali promoters are potassium, rubidium, cesium, or mixtures thereof. Especially preferred is potassium.

The catalyst precursor may then be dried at temperatures up to about 125° C. after which the precursor is calcined, that is, treated with an oxygen containing gas to convert the metal salts or metal compounds, as the case may be, to the oxide form. Calcining may be effected at temperatures ranging from about 150° C. to about 500° C., preferably about 250° C. to 400° C.

After calcination the material may be ground to any suitable size for use in either a slurry or fixed bed reactor. Particle sizes for a slurry process may range from 5 to about 100 microns, for fixed bed from about 100 to 500 microns.

The copper-alkali metal, promoted iron-zinc oxide catalyst is first subjected to a pretreatment procedure comprising exposure of the oxide to a reducing gas containing hydrogen, carbon monoxide or mixtures thereof. This procedure can be conducted in a separate vessel or in the Fischer-Tropsch synthesis reactor. Pretreatment in the reactor is preferred in order to eliminate the need for a potentially costly and sensitive transfer step to the olefin synthesis reactor. In situ pretreatment is especially preferred when operating the catalyst in a slurry reactor.

A preferred slurry pretreatment procedure involves suspending the catalyst in a relatively non-volatile hydrocarbon phase, introducing synthesis gas comprising hydrogen and carbon monoxide with an $H_2:CO$ molar ratio ranging from about 0.5/1 to about 3/1 into the two phase mixture and increasing the temperature up to 150°-350° C. so as to convert the catalyst to an active phase. The pretreatment can be conducted at pressures ranging from 1 to about 40 atm, the preferred pressure range being from 2 to about 20 atm.

The slurry Fischer-Tropsch synthesis process of the present invention may be conducted with from about 2 to about 30% wt or more of the catalyst suspended in a liquid phase. The liquid phase is usually comprised of an inert hydrocarbon that is relatively nonvolatile under reaction conditions. Representative materials include synthetic paraffins with 10 or more carbon atoms or higher molecular weight hydrocarbons generated from the synthesis gas conversion process. Other liquids such as high boiling alcohols, ethers, esters and the like can also be used without departing from the scope of this invention. The process is operated at temperatures ranging from about 200° C. to about 350° C., preferably from 250°-300° C. The pressure of the slurry process can range from 1 to about 40 atm, preferably from 5-20 atm. Synthesis gas containing from 0.5/1 to about 3/1 $H_2:CO$ molar ratios may be employed, preferably from about 1/1 to about 2/1. The synthesis gas feed rate can range from about 2,000 to about 30,000 vol feed gas per volume of catalyst per hour (v/v/h), preferably from about 5,000 to about 15,000 v/v/h. Under these conditions, the catalysts of the present invention exhibit olefin productivities that are three to five times higher than those previously disclosed. (Olefin productivity is defined as volumes of CO converted to olefins per volume of catalyst per hour.)

The Fischer-Tropsch synthesis process using the catalyst described herein produces primarily liquids, that is, the $C_5+/C_4-$ product ratio is at least about 4.5/1, preferably at least about 5/1 and usually about 5/1 to 10/1. Of the liquid product the olefin/paraffin ratio may range from about 2.5:1 or greater, usually 2.8:1 to 3.8:1, and the alpha olefin to internal ratio is at least about 10:1, usually 10:1 to greater than 50:1.

EXAMPLES

Catalyst Preparation

Example 1

Preparation of $Fe_{2.8}Zn_{0.2}O_4$ Spinel from Ammonium Glycolate Precursors

A solution of iron-zinc salts was prepared by mixing 100 cc of water containing 97.3 g of dissolved $Fe(NO_3))_3.9(H_2O)$ together with 10 cc of water containing 5.4 g of dissolved $Zn(NO_3)_2.x(H_2O)$ (30.2% $H_2O$). To 23.1 g of 85% glycolic acid, a sufficient amount of ammonium hydroxide was added (ca. 23 cc) to dissolve the glycolic acid and raise the pH to 6.5. This solution was added to the Fe-Zn nitrate solution and allowed to dry, during which a foaming amorphous product was formed. The material was then calcined in air for one hour at 350° C. X-ray diffraction showed this material to be a single phase spinel.

The spinel was promoted with 2% g-atom K and 1% g-atom Cu in the following manner. 7 g of the spinel was impregnated by incipient wetness with 0.124 g of $K_2CO_3$ dissolved in 14 cc of water. The resulting material was dried at 110° C., and then treated with 14 cc of water containing 0.22 g of $Cu(NO_3)_2.3(H_2O)$ by incipient wetness. The resulting material was dried in similar fashion.

Example 2

Preparation of Fe-Zn-O Catalyst with Fe:Zn of 14:1 by Ascending pH Precipitation A solution containing 5.38 g of $Zn(NO_3)_2-6(H_2O)$ and 97.3 g of $Fe(NO_3)_3-9(H_2O)$ in 110 cc of water was heated to 80° C. and a sufficient quantity of concentrated ca. 14M ammonium hydroxide was added to form a precipitate, while raising the final pH to 9. The precipitate was filtered, washed thoroughly with water and dried at 100° C. The resulting material was calcined in air at 350° C. for one hour. X-ray diffraction of this material indicated a corundum containing oxide phase.

(a) Promotion with 2% g-atom K 7 g of the oxide was treated with 0.124 g of $K_2CO_3$ dissolved in 2.8 cc of water by the incipient wetness impregnation procedure, the resulting material dried at 110° C.

(b) Promotion with 1% g-atom Cu 7 g of the oxide was treated with 0.22 g of $Cu(NO_3)_2-3(H_2O)$ dissolved in 2.8 cc of water by the incipient wetness impregnation procedure, the resulting material dried at 110° C.

(c) Promotion with 2% g-atom K and 1% g-atom Cu 7 g of the oxide was treated according to the procedure of Example 2(a) and the resulting material then treated with 0.22 g of $Cu(NO_3)_2-3(H_2O)$ dissolved in 2.8 cc of water by the incipient wetness impregnation procedure.

The resulting material was dried at 110° C.

Example 3

Preparation of Fe-Zn-O with Fe:Zn 14:1 by Controlled pH Precipitation

A 1M solution of $Fe^{+3}$ was prepared by dissolving 808 g of $Fe(NO_3)_3\text{-}9(H_2O)$ with water in a 2 liter volumetric flask. A 1M solution of $Zn^{+2}$ was prepared by dissolving 271 g of $Zn(NO_3)_2\text{-}x(H_2O)$ (30.2% $H_2O$) with water into a 1 liter volumetric flask. An iron-zinc nitrate solution was prepared by adding 105 cc of the 1M $Zn^{+2}$ solution to 2 liters of the 1M $Fe^{+3}$ solution. A 1M solution of ammonium carbonate was prepared by dissolving 192 g of $(NH_4)_2CO_3$ with water into a 2 liter volumetric flask.

The mixed iron-zinc nitrate solution was added at a rate of ca. 15 cc per minute via a controlled feed pump into a large flask which initially contained 300 cc of water. The contents of the large flask were continuously circulated through a centrifugal pump to achieve thorough mixing. The ammonium carbonate solution was fed through a second feed pump that was interfaced through a computerized controller. The ammonium carbonate solution flow was controlled to keep the pH of the well circulated slurry at a level of 7. Within 20-30 seconds of initiating this process, the pH reached a level of 7(+ or −0.2) and was maintained in this narrow range throughout the addition procedure which lasted 40-60 min. The resulting precipitate was washed thoroughly with water, dried at 110° C. overnight and calcined at 350° C. in air for one hour. X-ray analysis of the resulting material showed a corundum oxide phase to be present.

(a) Promotion with 2% g-atom K and 1% g-atom Cu 2.5 g of the oxide was treated with 0.045 g of $K_2CO_3$ dissolved in 1 cc of water by the incipient wetness impregnation procedure. The resulting material was dried at 110° C. followed by treatment with a solution of 0.083 g of $Cu(NO_3)_2\text{-}3(H_2O)$ in 1 cc of water by the incipient wetness impregnation procedure. The resulting material was then dried at 110° C.

Example 4

Preparation of $Fe_{2.3}Zn_{0.7}O_4$ Spinel From Ammonium Glycolate Precursors A solution was prepared containing 38.2 g of $Fe(NO_3)_3\text{-}9(H_2O)$ and 7.8 g of $Zn(NO_3)_2\text{-}x(H_2O)$ (30.2% $H_2O$) in 85 cc of water. To 10.1 g of 85% glycolic acid, a sufficient amount of ammonium hydroxide was added (ca. 23 cc) to raise the pH to 6.5. This solution was added to the Fe-Zn solution and then allowed to dry, thereby forming a foaming amorphous product. The resulting solid was calcined in air for one hour at 350° C. X-ray analysis indicated a single phase spinel had formed.

(a) Promotion with 2% g-atom K and 1% g-atom Cu

To 5 g of the spinel was added 8 cc of water containing 0.087 g of dissolved $K_2CO_3$ by the incipient wetness impregnation procedure followed by drying at 110° C. Following this, 0.16 g of $Cu(NO_3)_2\text{-}3(H_2O)$ dissolved in 8 cc of water was added by the incipient wetness impregnation procedure, the resulting material dried at 110° C.

Example 5

Preparation of $Fe_{2.45}Zn_{0.55}O_4$ From Ammonium Glycolate Precursors

A solution was prepared containing 84.8 g of $Fe(NO_3)_3\text{-}9(H_2O)$ and 13.37.8 g of $Zn(NO_3)_2\text{-}x(H_2O)$ (30.2& $H_2O$) in 115 cc of water. A solution of 20.4 g of 85% glycolic acid was prepared and sufficient ammonium hydroxide added to raise the pH to 6.5. This solution was added to the Fe-Zn solution and on drying led to the formation of a foaming amorphous product. The material was calcined in air for one hour at 350° C. X-ray analysis indicated the formation of a single phase spinel.

(a) Promotion with 2% g-atom K and 1% g-atom Cu

To 4 g of the spinel was added 8 cc of water containing 0.07 g of dissolved $K_2CO_3$ by the incipient wetness impregnation procedure followed by drying at 110° C. Following this, 0.12 g of $Cu(NO_3)_2\text{-}3(H_2O)$ dissolved in 8 cc of water was added by the incipient wetness impregnation procedure, the resulting material dried at 110° C.

Example 6

Effect of Fe:Zn Atomic Ratio on Catalyst Performance

A series of comparative performance tests were conducted with 2 g samples of each of the catalysts from Examples 1, 4(a) and 5(a). The individual catalyst was charged together with 72 g of octacosane to a 300 cc Parr CSTR reactor. Synthesis gas ($H_2$:CO=2:1) was introduced at a rate of 180 cc/min to the reactor at 75 psig and the temperature raised to 270° C. An additional 20 cc/min of nitrogen was fed to the reactor as an internal standard for subsequent analytical tests. The results of experiments conducted over 40–100+ hour periods are shown below for the respective catalyst systems.

| Catalyst | $Fe_{2.8}Zn_{0.2}O_4$ | $Fe_{2.55}Zn_{0.45}O_4$ | $Fe_{2.3}Zn_{0.7}O_4$ |
|---|---|---|---|
| % CO Conversion | 80 | 84 | 32 |
| % Carbon Selectivity to $CH_4$ | 1.7 | 1.7 | 2.3 |
| % Olefin in $C_2$-$C_4$ | 93 | 92 | 85 |
| % Alpha-Olefin in $C_{10}$ Fraction | 63 | 61 | (#) |

(#) This catalyst did not give meaningful yields of liquids at the conditions tested.

This data illustrates that the Fe:Zn ratio must be maintained at a level greater than 5:1 to obtain high activity and selectivity to $C_2$-$C_{10+}$ olefins.

Example 7

Effect of Dual K and Cu Promoters

Comparative tests of Fe:Zn 14:1 catalysts from Example 2(a), 2(b) and 2(c) were conducted in a 300 cc Parr CSTR to determine the effect of dual promoters on olefin synthesis performance under the test conditions used in Example 6. In each run listed below, a 2 g sample of catalyst was suspended in 72 g of octacosane and, after a 2-4 hour activation period, the runs were followed for a 40-100+ hour period.

| Catalyst | 2(c) | 2(a) | 2(b) |
|---|---|---|---|
| % g-atom K | 2 | 2 | 0 |

-continued

| Catalyst | 2(c) | 2(a) | 2(b) |
|---|---|---|---|
| % g-atom Cu | 1 | 0 | 1 |
| % CO Conversion | 73 | 33 | 34 |
| % Carbon Selectivity to $CH_4$ | 1.9 | 2.0 | 10.1 |
| Olefin/Paraffin Ratio in $C_4$ Fraction | 7.9 | 8.0 | 4.4 |

The results shown above illustrate that the K and Cu promoters must be present together in order to achieve the highest activity, lowest methane selectivity and highest olefin/paraffin ratio in a single catalyst system.

Example 8

Olefin/Paraffin Ratio from a Controlled pH Precipitated Catalyst

A 2.5 g sample of catalyst 3(a) was loaded into a 300 cc Autoclave Engineers CSTR together with 100 g of distilled (150+°C.) Fischer-Tropsch wax as a slurry solvent. The unit was equipped with an online capillary gc which was able to monitor products containing up to 10 carbon atoms. The reactor was maintained at a temperature of 270° C., 75 psig with 370 cc/min of a 2/1 $H_2/CO$ feed. The superficial space-velocity (v/v/h) based on an initial catalyst density of 1.8 g/cc was approximately 15,000 v/v/h. CO conversions in excess of 60% were maintained during the initial 80 hour test period, while methane selectivities of 4.5% ($CO_2$ free basis) was observed. The $C_{5+}$ selectivities with this catalyst is >75% on a $CO_2$ free basis. The olefin/paraffin ratios observed for the $C_2$-$C_{10}$ products measured at 81 hours on stream time are summarized below.

| Carbon Number | Olefin/Paraffin Ratio |
|---|---|
| 2 | 4.7 |
| 3 | 5.8 |
| 4 | 4.3 |
| 5 | 4.1 |
| 6 | 3.9 |
| 7 | 3.8 |
| 8 | 3.6 |
| 9 | 3.6 |
| 10 | 3.6 |

The data from the examples above shows that the Fe-Zn spinel and corundum containing catalysts with an Fe:Zn ratio>5, containing the dual K and Cu promoters in the levels defined in the instant invention, will provide a highly active, stable and selective catalyst for production of $C_2$-$C_{10+}$ olefins when conducted according to the process of the instant invention.

Earlier, the catalyst of Benbenek et al was referred to as having all of the components of the present invention. However, the Benbenek system does not contain copper and alkali metal in the proportions disclosed herein. Specifically, Benbenek operates with a catalyst comprising Fe:Cu:ZnO:$K_2O$ of 100:20:10:8, i.e., alkali:copper ratio <1:1 and a Cu:Zn ratio>1:1. At 300° C., 150 psi, 400 v/v/hr with 1:1 $H_2/CO$, the Benbenek system only gives 55% conversion (relative to 60% conversion at 15,000 v/v/hr with the catalytic process of the present invention) and >10% $CH_4$ (the catalyst of the present invention gives <5% $CH_4$). Another major difference in the performance of these catalysts is in $C_{5+}$ selectivity where the Benbenek catalyst produces <40% liquid products while the catalytic process of the instant invention generates >75% liquids. By carefully controlling the addition and relationship of promoters, the system disclosed herein achieves greater CO conversion rates than reported by Benbenek et al, as well as greater selectivity to olefins, all of which is accomplished at lower pressures and higher space velocities.

What is claimed is:

1. A composition comprising
   iron
   zinc
   copper
   an alkali metal selected from the group consisting of potassium, rubidium, cesium, or mixtures thereof, wherein
   the iron:zinc atomic ratio is at least about 5:1, and the alkali metal:copper atomic ratio is at least about 2:1.

2. The composition of claim 1 wherein the total alkali metal content of the composition is no greater than 6% g-atom, based on total metal content.

3. The composition of claim 2 wherein the alkali metal is potassium.

4. The composition of claim 1 wherein the iron and zinc are derived from spinel.

5. The composition of claim 1 wherein the iron is derived from a corundum phase.

* * * * *